United States Patent [19]

Orejola

[11] Patent Number: 4,637,380
[45] Date of Patent: Jan. 20, 1987

[54] SURGICAL WOUND CLOSURES

[76] Inventor: Wilmo C. Orejola, 1012 Black Oak Ridge Rd., Wayne, N.J. 07470

[21] Appl. No.: 748,035

[22] Filed: Jun. 24, 1985

[51] Int. Cl.$^4$ .......................... A61B 17/04; A61B 17/08
[52] U.S. Cl. .................................. 128/334 C; 128/335
[58] Field of Search ............ 227/DIG. 1; 128/334 R, 128/335, 337, 334 C, 329, 339; 273/33, 202, 206, 212; 604/117

[56] References Cited

U.S. PATENT DOCUMENTS

| | | | |
|---|---|---|---|
| 3,068,869 | 12/1962 | Shelden et al. | 128/337 |
| 3,825,010 | 7/1974 | McDonald | 128/337 |
| 4,467,805 | 8/1984 | Fukuda | 128/334 R |

Primary Examiner—Richard C. Pinkham
Assistant Examiner—Gary Jackson
Attorney, Agent, or Firm—Linval B. Castle

[57] ABSTRACT

A surgical wound closure in which none of the closure elements contact the wound surface includes a pair of flexible and pliable plastic skeleton rods having facing surfaces connectable together by alternate buttons and sockets. The outer surfaces of the rods support a plurality of pins that extend outward and downward to a position below the lower surface of the interconnected rods and which then terminate in inward curved sharpened points for engaging the skin about 8 mm each side of the wound edges. Each pin is provided with a plastic coating which ends short of the curved point to serve as a stop to limit the insertion of the pin.

5 Claims, 5 Drawing Figures

SURGICAL WOUND CLOSURES

This invention relates generally to surgical sutures and particularly to novel wound closures comprising a pair of rods each having a plurality of pins for engaging the skin along each side of a wound and having facing connector buttons and sockets for intercoupling the strips above the surface of the wound.

BRIEF SUMMARY OF THE INVENTION

The conventional method of closing surgical wounds is by the use of silk or wire staple sutures applied by stitching together the lips of the wound. While quite adequate, this method of closure requires a substantial amount of the surgeon's time and often results in crisscross keloids and objectionable cosmetic blemishes in the skin tissues around the area of the wound.

There is need for a surgical closure that can be rapidly and accurately applied in a minimum of time and without actually contacting the wound surface. The closure described herein provides such need.

It is the principal object of the invention to provide a wound closure device for rapidly and accurately closing the edges of an open wound.

A second important object of the invention is to provide a wound closure that will accurately and securely close a wound without contacting the wound.

Another important object of the invention is to provide a wound suturing means that provides precise coaption of the wound edges to result in a clean and often invisible scar.

Briefly described, the surgical wound closure of the invention comprises first and second identical plastic skeleton rods each having connected thereto a plurality of stainless steel pins extending outward and downward below the lower surface of the rod and bending inward to a very sharp point, the pins on each rod engaging a line of skin about eight millimeters from the wound. The facing parallel surfaces of the plastic rods have alternately spaced button and socket connectors for interconnecting the two rods after the pins are properly placed. Thus, the proper placing of the pins and the interconnecting of the two parallel skeleton rods will accurately close the wound with the rods elevated thereabove, and will secure the wound closure until the rods are later separated and the pins removed from the surrounding skin.

DESCRIPTION OF THE DRAWINGS

In the drawings which illustrate the preferred embodiment of the invention.

DETAILED DESCRIPTION OF THE PREFERRED EMBODIMENT

Figure 1:
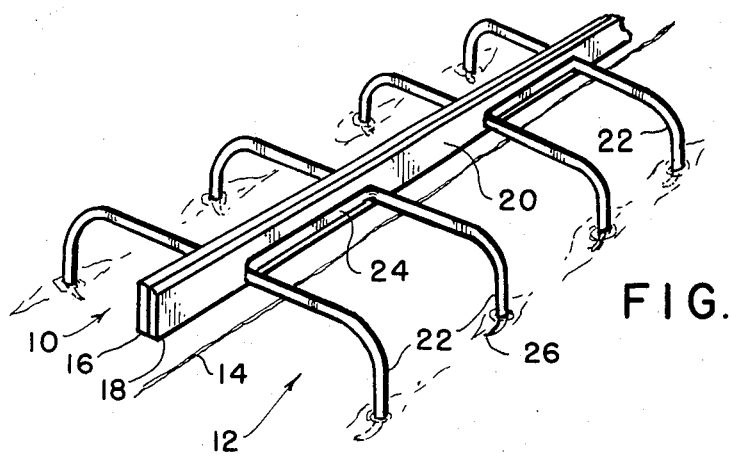
FIG. 1 is a perspective drawing illustrating a portion of the coupled wound closures over the closed edges of a wound.

FIG. 1 is a perspective view illustrating a pair of the wound closures 10, 12 of the invention interconnected over a closed wound 14. Each of the closures are identical and each includes a relatively long skeleton rod 16 and 18 of a pliable plastic, such as polyethylene, having a typical dimension of 3 mm. wide, 6 mm high and of any convenient length from which any required portion may be cut. Because of the flexibility of the skeleton rods, they may be readily cut to desired lengths and easily bent to conform to curved wounds.

Each of the plastic skeleton rods 16, 18 has, on its outer surface 20, a plurality of pins 22 for engaging the skin along a line parallel with and on each side of the wound edges. The pins are preferably formed of a strong surgical stainless steel and in pairs with an interconnecting section 24 which is firmly cemented to, or imbedded into the skeleton surface 20. From the section 24, each pin extends outward approximately 5 mm and downward approximately 6 mm at which point it is curved back inward toward the wound about 1 mm to terminate in a very sharp point 26 for engaging the skin about 8 mm each side of the wound edges.

Figure 2:
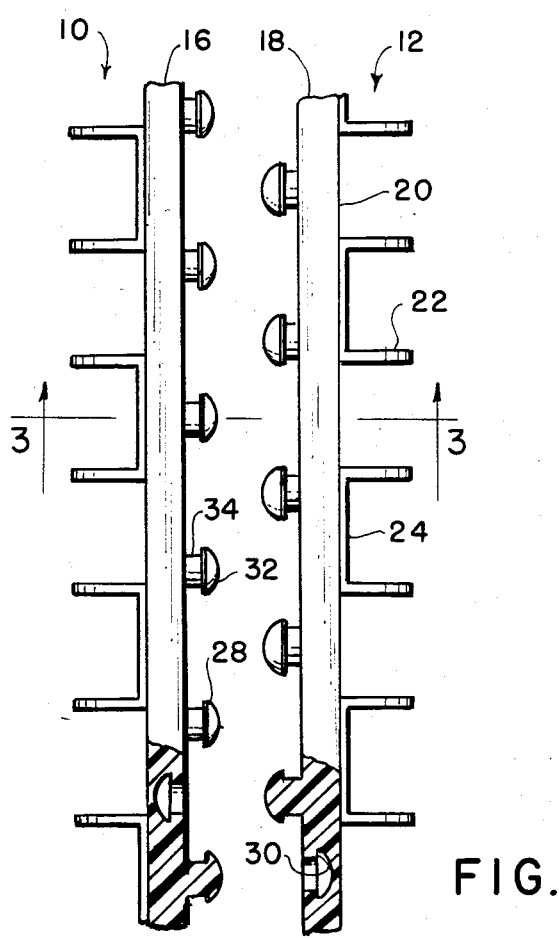
FIG. 2 is a top plan view of the wound closure strips illustrating, in section, the button and socket skeleton rod connectors.

After the points 26 on each of the two plastic skeleton rods 16, 18 are properly attached, the two skeletons are pressed together and interconnected to thereby draw together the wound for precise coaption of the wound and edges 14. FIG. 2 is a plan view illustrating the wound closure strips 10 and 12 and the structure of the plastic skeleton rods 16 and 18 that enables their interconnection.

Each of the closure elements or strips 10 and 12 are identical as previously mentioned and have, centered along their flat interior surfaces, a plurality of alternately and equally spaced buttons 28 and sockets 30. Each button has a mushroom shape and preferably has a truncated spherical or conical section 32 at the end of a short thin neck section 34 that extends at right angles from the planar inner surface and forms an integral part of the pliable plastic skeleton rod. Each socket 30 is an opening in the interior face of the skeleton and provides a button-matching configuration into whith a button may be pressed and held against easily removal as illustrated in FIG. 2. To eventually separate the two interconnected closure strips, it is only necessary to pry them apart with a thin blade or grasp oppositely positioned pins with a clamp or the like.

Figure 3:
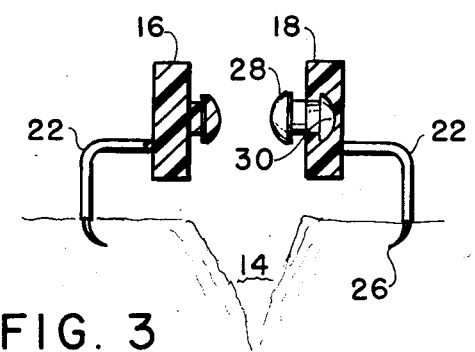
FIG. 3 is a sectional view taken along the lines 3—3 of FIG. 2.
Figure 5:
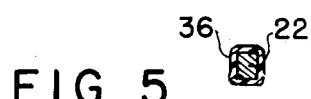
FIG. 5 is a sectional view of a pin taken along the lines 5—5 of FIG. 4.
Figure 4:
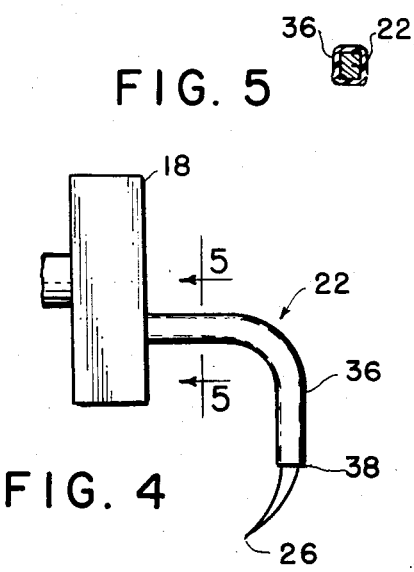
FIG. 4 is a detailed view illustrating the configuration of the pins mounted along the outer surface of each plastic skeleton rod.

FIG. 3 is a sectional end view of the two closures 10 and 12 as taken along the lines 3—3 of FIG. 2, and illustrates ther mushroom shaped buttons 28 and sockets 30 at the inner surface of the skeleton rods 16, 18, and the sharpened pins 22 connected near the lower edge of the outer surface of the skeleton. It will be noted in FIG. 3 and in the enlarged biew of FIG. 4 that the pins 22 are preferably coated with a plastic coating 36 that extends from the outer surface of the skeleton to the point 38 where the sharpened points of the pins are bent inward to engage the patient's skin. The plastic coating 36 at the point 38 provides a predetermined stop that limits the extent of introdermal engagement of the sharp pin points 26. FIG. 5 is a sectional view taken along lines 5—5 of FIG. 4 and illustrates the stainless steel pin with its plastic coating 36.

A very important feature of the invention is illustrated in FIG. 3. The pins 22 extend outward and downward approximately 6 mm to the end-of-coating point 38 which is located approximately 4 mm below the bottom level of the skeletons. Thus, the bottom surfaces of the skeleton rods are elevated about 4 mm above the surface of the patient's skin and the top surfaces of the wound 14 with the result that no part of the wound closure strips can become in contact with the wound.

While the wound closures of the invention may be used in any convenient manner, a preferred method is to first draw a line along the surface of the patient's skin at which the incision is to be made, and then draw parallel lines 8 mm on both sides of the incision line. Later, when the incision is to be closed, the points 26 on both closure rods will engage their respective outer lines, care being taken to assure that the buttons on one skeleton rod are properly aligned with the sockets on the other rod. The wound is then pressed closed and the two wound closure rods are interconnected to accurately hold together the wound edges for precise coaption and without the danger of keloids that often result from conventional silk or steel wire suturing.

What I claim is:

1. A wound closure comprising:
    a pair of skeleton rods, each rod having a substantially planar inner surface, an outer surface opposite said inner surface, and a bottom surface;
    a plurality of pins connected to the outer surface of each of said pair of rods, each pin extending outward from said outer surface and downward to a predetermined position below the level of said bottom surface and thence in an inward turning bend toward the wound to terminate in a short sharpened point for engaging the skin of a patient, each pin of said plurality being coated with a plastic coating between its respective skeleton rod and a predetermined position below the level of said bottom surface, said predetermined position forming a stop for limiting the length of insertion of said sharpened pin points; and
    means for interconnecting said planar inner surfaces of said pair of skeleton rods.

2. The closure claimed in claim 1 wherein each of said pair of skeleton rods are formed of a flexible and pliable plastic material.

3. The closure claimed in claim 2 wherein said interconnecting means includes a plurality of alternate and evenly spaced buttons and sockets formed in the inner surface of each skeleton rod, each button being an enlarged pliable plastic section at the end of a short thin neck connected to said inner surface, each socket being an opening in said inner surface and substantially conforming to the configuration of said button.

4. The closure claimed in claim 1 wherein said plurality of pins are formed in pairs with each pair having an interconnecting section attached to the outer surface of each of said pair of skeleton bars.

5. The closure claimed in claim 4 wherein said pins are formed of stainless steel.

* * * * *